United States Patent [19]
Moriniere et al.

[11] Patent Number: 5,212,161
[45] Date of Patent: May 18, 1993

[54] DERIVATIVES OF 2'-DEOXYURIDINE SUBSTITUTED IN THE 5-,3'-OR 5'-POSITION BY α-AMINACYL GROUPS, PROCESS FOR THEIR PREPARATION AND DRUGS IN WHICH THEY ARE PRESENT

[75] Inventors: Jean-Luc Moriniere, Neauphle le Chateau; Michelle Faulques, Paris; Claude Rousseau, Orgerus; Bernard Danree, Poissy; Claude Marquer, Chatou; Patrick Saur, Chevilly la Rue; Jean Lemoine, Bougival; Jean-Yves Lacolle, Saint Nom la Breteche, all of France

[73] Assignee: Institut de Recherches Chimiques et Biologiques Appliquees (I.R.C.E.B.A.), France

[21] Appl. No.: 566,344

[22] PCT Filed: Feb. 23, 1989

[86] PCT No.: PCT/FR89/00072

§ 371 Date: Aug. 17, 1990

§ 102(e) Date: Aug. 17, 1990

[87] PCT Pub. No.: WO89/08115

PCT Pub. Date: Sep. 8, 1989

[30] Foreign Application Priority Data

Feb. 24, 1988 [FR] France .................. 88 02255
Jun. 28, 1988 [FR] France .................. 88 08684

[51] Int. Cl.$^5$ .................. A61K 31/70; C07H 17/00
[52] U.S. Cl. .................. 514/50; 536/28.2; 530/327
[58] Field of Search .................. 536/23, 24; 514/50, 514/14, 15, 16, 17, 18; 530/327-330

[56] References Cited

U.S. PATENT DOCUMENTS 3,853,845 12/1974 Rousseau et al.
4,093,716 6/1978 Lin et al.
4,128,639 12/1978 Lin et al.

FOREIGN PATENT DOCUMENTS

WO88/00201 1/1988 World Int. Prop. O. .......... 536/23

OTHER PUBLICATIONS

The Merck Index (1967) pp. 872-873.
Chem. Pharm. Bull. 25(7) 1740-1748 Azuna et al. (1977).
CA 117(5):49132t (1992) Wengel et al.
"Synthesis and Biological Activity of Several Amino Analogues of Thymidine", Linn et al., Journal of Medicinal Chemistry, 1978, vol. 21, No. 1, pp. 109-112.
"Studies on the Action of Thymidine Analogues", Beltz et al., Journal of Biological Chemistry, vol. 226, pp. 1035-1045, 1957.
"Nucleoside Peptides. I. The Synthesis of 5'-Deoxy-5-'-amino-5'-N-aminoacyl Peptide Derivatives of Guanosine, Adenosine, and 2'-Deoxyadenosine and Their Effect on Cell-Free Protein Synthesis", Robbins et al., J. Am. Chem. Soc., vol. 6, 1971, pp. 1474-1480.
"Nucleosides. I. 5'-Amino-5'-Deoxyuridine and 5'-Amino-5'-deoxythymidine", Horwitz et al., J. Org. Chem., 27, pp. 3045-3048.
Design of Species–or Isozyme-Specific Enzyme Inhibitors, 1. Effect of Thymidine Substitutents on Affinity for the Thymidine Site of Hamster Cytoplasmis, Thymidine Kinase, Hampton et al., J. of Org. Chem., 22, No. 6, pp. 621-631 (1979).

Primary Examiner—Johnnie R. Brown
Assistant Examiner—A. Varma
Attorney, Agent, or Firm—Lerner, David, Littenberg, Krumholz & Mentlik

[57] ABSTRACT

The present invention relates to novel derivatives of 2'-deoxyuridine substituted in the 5-, 3'- or 5'-position by α-aminoacyl groups, to a process for their preparation and the drugs in which they are present.

These derivatives have the following general formula:
(Abstract continued on next page.)

5 Claims, No Drawings

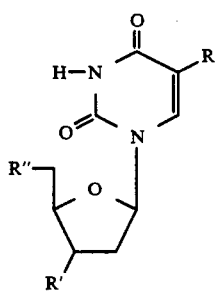

in which
R is selected from an alkyl or alkenyl radical having from 1 to 4 carbon atoms, an aryl radical or a halogen, it being possible for said alkyl, alkenyl and aryl radicals to contain at least one halogen substituent, and a radical of the formula —NH—$R_1$, in which $R_1$ is an amino acid residue or a peptide residue containing from 2 to 6 amino acids; and R' and R" are selected from a hydroxyl radical and a radical of the formula —NH—$R_1$, in which $R_1$ is as defined above, with the proviso that R' and R" are not simultaneously —NH—$R_1$ and that, when R is —NH—$R_1$, R' and R" are simultaneously a hydroxyl group.

Application: treatment of cancers and viral infections.

DERIVATIVES OF 2'-DEOXYURIDINE SUBSTITUTED IN THE 5-,3'-OR 5'-POSITION BY α-AMINACYL GROUPS, PROCESS FOR THEIR PREPARATION AND DRUGS IN WHICH THEY ARE PRESENT

BACKGROUND OF THE INVENTION

The present invention relates to novel derivatives of 2'-deoxyuridine substituted in the 5-, 3'- or 5'-position by a α-aminoacyl groups, to a process for their preparation and to pharmaceutical compositions in which they are present.

Some 2'-deoxyuridine derivatives are already known.

Thus derivatives of 2'-deoxyuridine substituted in the 5-position have been described which have the following general chemical formula:

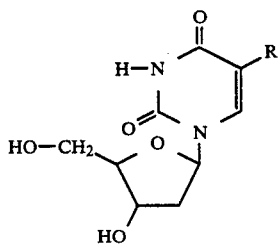

in which
R is an alkyl or alkenyl radical having from 1 to 4 carbon atoms, an aryl radical or a halogen, it being possible for said alkyl and aryl radicals to contain at least one halogen substituent.

5'-Amino-2', 5'-dideoxy-5-methyluridine of the formula:

is also known, especially from U.S. Pat. No. 4,093,716; it is presented as a potential inhibitor of the herpes virus. The preparation of this compound is described in an article by Horwitz et al. in the journal "J. Org. Chem." 27 3045, (1962).

3'-Amino-2',3'-dideoxy-5-methyluridine of the formula:

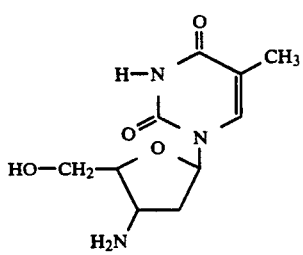

is also known, especially from a publication by LIN and PRUSOFF (J. Med. Chem. 21 109 (1978)).

Finally, 5-amino-2'-deoxyuridine of the formula:

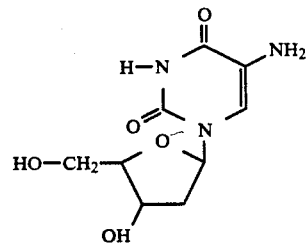

is known, especially from a publication by BELTZ and VISSER (J. Biol. Chem., 226, 1035, (1957)). The document J. Med. Chem. 1979, vol. 22, No. 6, pages 621 to 631 describes in general terms a process for the preparation of 5-[[ω-(iodoacetamido)acyl]amino]-2'-deoxyuridines using, as synthesis intermediates, compounds of the formula:

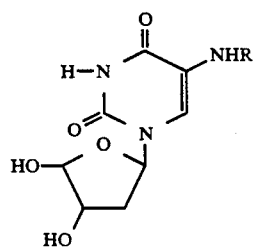

in which R is the residue of an ω-amino acid.

These compounds are not presented as being capable of therapeutic application.

The present invention relates to a novel class of derivatives of 2'-deoxyuridine substituted in the 5-, 3'- or 5'-position by α-aminoacyl groups, which have the following general formula:

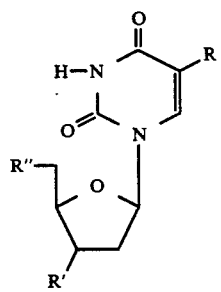

(I)

in which
R is selected from an alkyl or alkenyl radical having from 1 to 4 carbon atoms, an aryl radical or a halogen, it being possible for said alkyl, alkenyl and aryl radicals to contain at least one halogen substituent, and a radical of the formula —NH—$R_1$, in which $R_1$ is an amino acid residue or a peptide residue containing from 2 to 6 amino acids; and
R' and R" are selected from a hydroxyl radical and a radical of the formula —NH—$R_1$, in which $R_1$ is as defined above,
with the proviso that R' and R" are not simultaneously —NH—$R_1$ and that, when R is —NH—$R_1$, R' and R" are simultaneously a hydroxyl group, and to their pharmaceutically acceptable salts.

The scope of the invention also includes all the possible optical isomers of the compounds of formula (I) and mixtures thereof.

In general formula (I), a halogen atom is preferably a chlorine or bromine atom.

The alkyl and alkenyl groups can be groups with a linear or branched chain.

An alkyl group having from 1 to 4 carbon atoms is, for example, a methyl, ethyl, propyl, isopropyl, butyl, sec-butyl or tert-butyl group, preferably a methyl or ethyl group.

An alkenyl group having from 1 to 4 carbon atoms is, for example, a vinyl, propenyl or butenyl group, preferably a vinyl group.

The pharmaceutically acceptable salts of the compounds of formula (I) include those formed with a mineral acid, for example hydrochloric acid or sulfuric acid, or with an organic acid, for example citric, tartaric, malic, maleic or fumaric acid.

It has been discovered, totally surprisingly, that these novel derivatives possess the valuable pharmacological property of being inhibitors of the fetal thymidine kinase present in human cancerous tissues and are thus inhibitors of DNA synthesis in proliferating cancerous cells.

According to one particular characteristic, the invention relates to the novel class of derivatives of 2'-deoxyuridine substituted in the 5'-position, i.e. the compounds of general formula (I) in which R' is a hydroxyl group and R'' is a group —NH—$R_1$.

According to another particular characteristic, the invention relates to the novel class of derivatives of 2'-deoxyuridine substituted in the 3'-position, i.e. the compounds of general formula (I) in which R' is a group —NH—$R_1$ and R'' is a hydroxyl group.

According to yet another particular characteristic, the invention relates to the novel class of derivatives of 2'-deoxyuridine substituted in the 5-position, i.e. the compounds of general formula (I) in which R is a group —NH—$R_1$ and R' and R'' are simultaneously hydroxyl groups.

Depending on the structure of the amino acid or peptide mentioned above, the novel compounds of formula (I) according to the invention are in the D, L or DL foam.

The general process for the preparation of the compounds according to the invention of general formula (I) as defined above comprises reacting an amine derivative of the general formula:

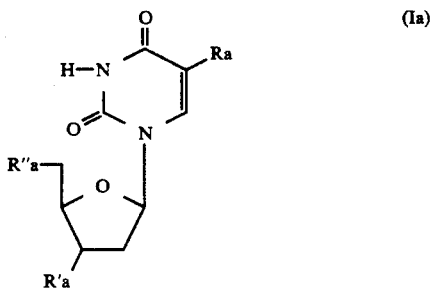

(Ia)

in which $R_a$ is selected from an alkyl or alkenyl radical having from 1 to 4 carbon atoms, an aryl radical or a halogen, it being possible for said alkyl, alkenyl and aryl radicals to contain at least one halogen substituent, and a radical —$NH_2$; and $R'_a$ and $R''_a$ are selected from a hydroxyl radical and a radical —$NH_2$, with the proviso that $R'_a$ and $R''_a$ are not simultaneously —$NH_2$ and that, when $R_a$ is —$NH_2$, $R'_a$ and $R''_a$ are simultaneously a hydroxyl group, with an amino acid or a peptide containing from 2 to 6 amino acids, by an enzymatic or chemical method, and, if desired, converting a compound obtained in this way into a pharmaceutically acceptable salt.

The compounds of L form are preferably prepared by enzymatic reaction of the amine derivatives of formula (Ia) with an amino acid or a peptide of L or DL form, in the presence of an enzyme selected from papain and chymopapain, the reaction being carried out at a temperature of about 10° to about 70° C. in an acid medium. Under these conditions, a reaction takes place between the amine group of the amine derivative in the 5-, 3'- or 5'-position and the free acid group of the amino acid or peptide, it being understood that the amine groups of said amino acid or peptide have been blocked beforehand with known reagents such as benzyloxycarbonyl, paramethoxybenzyloxycarbonyl, t-butoxycarbonyl or fluorenomethoxycarbonyl.

The compounds of L, D or DL form can also be prepared using a purely chemical process, which may involve the separation of a mixture of isomers of the compounds of formula (I) into the isolated isomers.

Surprisingly, the compounds of formula (I) according to the invention were found to be active in inhibiting DNA synthesis in cancerous cells and certain viral particles.

These compounds are therefore especially useful in the treatment of hormone-dependent cancers and infections of viral origin.

Oral administration is generally employed for all conditions requiring such compounds. For this purpose, the compounds of the invention can be administered at doses for example of between about 30 mg/m² and about 100 mg/m² per day in the treatment of cancers and for example of between about 50 mg/kg and about 250 mg/kg per day in the treatment of infections of viral origin. Of course, these dosages can be adjusted to ensure the optimum therapeutic response.

Thus, according to a final feature, the present invention relates to pharmaceutical compositions, especially those active as inhibitors of DNA synthesis in proliferating cancerous cells, which contain, as the active ingredient, at least one of the above-defined compounds of general formula I in association with a pharmaceutically acceptable, non-toxic vehicle or carrier.

The pharmaceutical compositions of the invention are generally prepared by conventional processes and are administered in an appropriate pharmaceutical form; for example, a solid oral form can contain, together with the active compound, diluents, for example lactose or cellulose; lubricants, for example stearic acid or polyethylene glycols; binders such as starches or methyl cellulose; colorants; sweeteners; wetting agents such as, for example, polysorbates; and, in general, non-toxic and pharmacologically inert substances used in pharmaceutical compositions.

The invention will be illustrated in greater detail by the following non-limiting Examples:

EXAMPLE 1

Enzymatic method

Synthesis of 5'-N-(L-alanyl)amino-2',5'-dideoxy-5-methyluridine

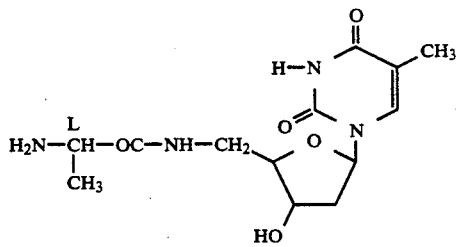

Step A: Synthesis of 5'-N-[(N-benzyloxycarbonyl)-L-alanyl]amino-2',5'-dideoxy-5-methyluridine The following are introduced successively into a 100 ml three-necked flask equipped with a magnetic stirrer, a thermometer and a condenser:
16 ml of normal sodium hydroxide solution
3.57 g of (N-benzyloxycarbonyl)-L-alanine (0.016 mol)
3.86 g of 5'-amino-2',5'-dideoxy-5-methyluridine (0.016 mol)
188 mg of L-cysteine hydrochloride dissolved in 2.4 ml of distilled water
20 ml of citric buffer solution of pH 5

The reaction medium, which has a pH of 8.98, is heated to 50° C.; the mixture is clear above 30° C.

At 50° C., a solution of 3.6 g of papain (2.9 IU/mg) in 8 ml of water is added. The pH changes slowly to 8.41.

The pH is brought to 4.6 by the addition of powdered citric acid (m=1.2 g) and the mixture is stirred vigorously for 24 h.

When the reaction is complete, the reaction medium is cooled and the precipitate is filtered off and washed with water.

After drying at 60° C. under vacuum, 4.3 g of 5'-N-[(N-benzyloxycarbonyl)-L-alanyl]amino-2',5'-dideoxy-5-methyluridine are obtained.

Purification is effected by crystallization from 50 ml of methanol.

| m = 3.9 g | Yield = 55% | Purity: 95% |

Step B:
This compound is dissolved in methanol and hydrogenated in the presence of 400 mg of 10% palladium-on-charcoal.

After filtration of the catalyst and concentration of the solvent, the residue is taken up with ethyl ether and the precipitate obtained is filtered off.

After drying, 7.9 mmol of 5'-N-(L-alanyl)amino-2',5'-dideoxy-5-methyluridine are obtained (Yield: 90%). Recrystallization of the above product from 20 ml of methanol gives 7.11 mmol of the desired compound in optically pure form. m=2.21 g; Overall yield: 44%; M.p.=190°–193° C. (Thermovar); $[\alpha]_D^{20}$=+28.5° (C=0.5 MeOH); IR (KBr): 1670 cm$^{-1}$ (C=O); 1275 cm$^{-1}$, 1580 cm$^{-1}$, 3250 cm$^{-1}$ (N-H). NMR (200 MHz, CD$_3$OD): 1.30 (3H, d, Me ala); 1.90 (3H, s, Me); 2.22 to 2.28 (2H, m, C-2'-H); 3.47 to 3.51 (3H, m, C-5'-H, C-ala-H); 3.90 to 3.92 (1H, m, C-4'-H); 4.25 to 4.27 (1H, m, C-3'-H); 6.18 (1H, t, C-1'-H); 7.49 (1H, s, C-6-H).

EXAMPLE 2

Chemical method

Synthesis of 5'-N-(D-alanyl)amino-2',5'-dideoxy-5-methyluridine

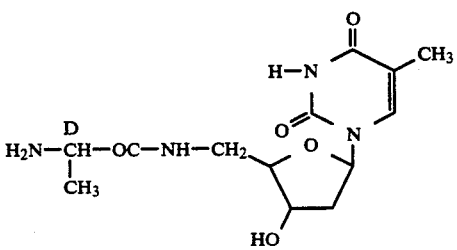

Step A: Synthesis of 5'-N-[(N-benzyloxycarbonyl)-D-alanyl]amino-2',5'-dideoxy-5-methyluridine.

The following are introduced into a 100 ml three-necked flask equipped with a magnetic stirrer, a thermometer and a calcium chloride drying tube:
20 ml of dry methylene chloride (4 Å sieve)
893 mg of (N-benzyloxycarbonyl)-D-alanine (4 mmol)
0.6 ml of triethylamine (4.3 mmol)

The solution obtained is cooled to −5° C. and 0.4 ml of ethyl chloroformate (4.2 mmol) is added.

After stirring for 90 minutes, 964 mg of 5'-amino-2',5'-dideoxy-5-methyluridine are added and the mixture is left for 60 minutes at −5° C. and then overnight at room temperature.

The precipitate formed is filtered off and washed with 15 ml of softened water. After drying in an oven under vacuum at 60° C., 1.33 g of 5'-N-[(N-benzyloxycarbonyl)-D-alanyl]amino-2',5'-dideoxy-5-methyluridine are obtained. Crystallization from 50 ml of methanol gives 1.2 g of a compound of satisfactory purity (Yield: 67%).

Step B:

Hydrogenolysis and purification analogous to those described in Example 1 yield optically pure 5'-N-(D-alanyl)amino-2',5'-dideoxy-5-methyluridine [m=715 mg; 2.3 mmol; Yield 57%]; M.p.=180°–184° C. (Thermovar); $\alpha_D^{20}$=+22.6° (C=1, MeOH); IR (KBr): 1670 cm$^{-1}$ (C=O); 1275 cm$^{-1}$, 1580 cm$^{-1}$, 3250 cm$^{-1}$ (N—H); TLC: (MeOH, H$_2$O: 80/20) rf=0.21 60 F$_{254}$ silica.

NMR (200 MHz, D$_2$O): 1.23-1.30 (3H, d, Me ala); 1.90 (3H, s, Me); 2.35 to 2.41 (2H, m, C-2'-H); 3.52 to 3.57 (3H, m, C-5'-H, C ala-H); 4.02 to 4.04 (1H, m, C-4'-H); 4.37 to 4.40 (1H, m, C-3'-H); 6.25 (1H, t, C-1'-H); 7.48 (11H, s, C-6-H)

EXAMPLE 3

Synthesis of
3'-N-(D-alanyl)amino-2',3'-dideoxy-5-methyluridine

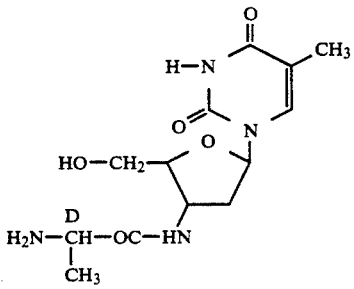

The operating protocol is identical to that described in Example 2.

Step A: Synthesis of 3'-N-[(N-benzyloxycarbonyl)-D-alanyl]amino-2',3'-dideoxy-5-methyluridine (1)

The starting materials are as follows:

20 ml of dry methylene chloride (4 Å sieve)

925 mg of (N-benzyloxycarbonyl)-D-alanine (4.15 mmol)

0.62 ml of triethylamine (4.4 mmol)

This gives 0.95 g of compound (1) with a satisfactory purity (Yield: 64%).

M.p. = 124°–128° C. (thermovar); $\alpha_D^{20} = +25°$ (c=0.1, MeOH) NMR (200 MHz, CD$_3$OD): 1.2 to 1.3 (3H, d, Me, ala); 1.7 (3H, s, Me); 2.29 to 2.32 (2H, m, C-2'-H); 3.7 to 3.9 (3H, m, C-5'-H, C-4'-H); 4 to 4.1 (1H, d, C-ala H); 6.2 (1H, t, C-1'-H); 7.3 to 7.4 (5H, m); 7.9 (1H, s, C-6-H)

Step B:

This compound (1) is dissolved in methanol and hydrogenated in the presence of 200 mg of 10% palladium-on-charcoal.

After filtration of the catalyst and concentration of the solvent, the residue is taken up with ethyl ether and the precipitate obtained is filtered off.

502 mg of 3'-N-(D-alanyl)amino-2',3'-dideoxy-5-methyluridine are obtained after drying (Yield 90%);

M.p. = 182°–184° C.

$\alpha_D^{20} = +22.5°$ (C=1, H$_2$O)

TLC: (MeOH, H$_2$O: 80/20) rf=0.26 60 F$_{254}$ silica

NMR (200 MHz, D$_2$O): 1.2 to 1.3 (3H, d, Me-ala); 1.9 (3H, s, Me); 2.4 (2H, m, C-2'-H); 3.7 (1H, m, C-ala); 3.8 to 3.9 (2H, m, C-5'-H); 4 (1H, m, C-4'-H); 4.4 to 4.6 (1H, m, C-3'-H); 6.2 to 6.3 (1H, t, C-1'-H); 7.7 (1H, s, C-6-H)

EXAMPLE 4

Chemical method

Synthesis of
3'-N-(L-alanyl)amino-2',3'-dideoxy-5-methyluridine

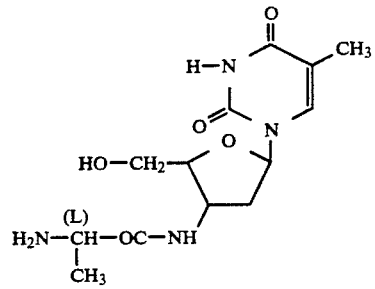

The operating protocol is identical to that described in Example 2.

Step A: Synthesis of 3'-N-[(N-benzyloxycarbonyl)-L-alanyl]amino-2',3'-dideoxy-5-methyluridine (2)

5 g (20.7 mmol) of 3'-amino-2',3'-dideoxy-5-methyluridine are used as the starting material.

This gives 6.14 g (13.7 mmol) of compound (2) with a satisfactory purity (Yield: 66.5%).

M.p. (thermovar): 145°–148° C.

$[\alpha]_D^{20} = +5.9°$ (c=1, MeOH)

NMR (200 MHz, CD$_3$OD): 1.30 to 1.34 (3H, d, Me-ala); 1.68 (3H, s, C-5-H); 2.28 to 2.34 (2H, t, C-2'-H); 3.7 to 3.8 (3H, m, C-4'-H, C-5'-H); 4.07 to 4.11 (1H, m, C-); 4.47 to 4.51 (1H, m, C-3'-H), 5.07 (2H, s, CH$_2$); 6.19 to 6.22 (1H, t, C-1'-H); 7.27 to 7.33 (5H, m, C$_6$H$_5$); 7.87 (1H, s, C-6-H)

Step B 3.66 g (11.7 mmol) of 3'-N-(L-alanyl)amino-2',3'-dideoxy-5-methyluridine are obtained from compound (2)

(Yield: 85.9%).

M.p. (thermovar): 180°–185° C.

$[\alpha]_D^{20} = +32.4°$ (C=1, MeOH)

NMR (200 MHz, D$_2$O): 1.28 to 1.31 (3H, d, Me-ala); 1.90 (3H, s, C-5-H); 2.41 to 2.50 (2H, m, C-2'-H); 3.54 to 3.58 (1H, m, C-ala H); 3.76 to 4.00 (3H, m, C-4'-H, C-5'-H); 4.49 to 4.53 (1H, m, C-3-H); 6.22 to 6.26 (1H, t, C-1'-H); 7.70 (1H, s, C-6-H)

EXAMPLE 5

Chemical method

Synthesis of 5-N-(L-alanyl)amino-2'-deoxyuridine

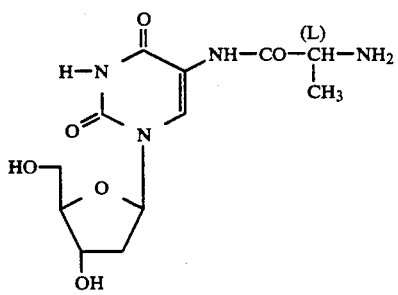

Step A: Synthesis of 5-N-[(N-benzyloxycarbonyl)-L-alanyl]amino-2'-deoxyuridine (3)

10.38 g (42 mmol) of N-(ethoxycarbonyl)-2-ethoxy-1,2-dihydroquinoline and 9.36 g (42 mmol) of (N-benzyloxycarbonyl)-L-alanine are added to a solution of 6 g (21 mmol) of 5-amino-2'-deoxyuridine hydrochloride in 220 ml of methanol and water (4:1) and 2.8 ml of triethylamine.

The reaction medium is kept at room temperature for 12 hours. After evaporation of the solvents under vacuum at 20° C., the oil obtained is carefully triturated in the presence of petroleum ether until a paste is obtained. The addition of chloroform produces a precipitate which, after filtration, is carefully washed several times with chloroform and finally with ether.

After drying under vacuum at 20° C., 8 g (18 mmol) of 5-N-[(N-benzyloxycarbonyl)-L-alanyl]amino-2'-deoxyuridine are obtained. Recrystallization from a mixture of chloroform and methanol gives 7.2 g (16.5 mmol) of a compound of satisfactory purity (Yield: 77%).

Purity (HPLC): 100%
$[\alpha]_D^{20} = -30°$ (C=0.5, MeOH)
M.p. (thermovar)=104°-107° C.
TLC 60 $F_{254}$ silica (CHCl$_3$, EtOH: 90/10) rf=0.176
NMR (200 MHz, CD$_3$OD): 1.36 to 1.39 (3H, d, CH$_3$ ala); 2.23 to 2.26 (2H, m, C-2'-H); 3.72 to 3.74 (2H, d, C-5'-H); 3.91 to 3.93 (1H, m, C-4'-H); 4.31 to 4.35 (2H, m, C-3'-H, CH-ala); 6.29 to 6.36 (1H, t, C-1'-H); 8.61 (1H, s, C-6-H)

Step B 4 g (9 mmol) of compound (3) are dissolved in 300 ml of methanol and hydrogenated in the presence of 400 mg of 10% palladium-on-charcoal for 3 hours. After filtration of the catalyst and concentration of the solvent, the residue is taken up with ethyl ether and the precipitate obtained is filtered off. 2.7 g (8.6 mmol) of 5-N-(L-alanyl)amino-2'-deoxyuridine are obtained after drying (Yield: 94%). Recrystallization from n-butanol gives 2.1 g (6.7 mmol) of the desired compound (Yield=73%).

Overall Yield: 56%
Purity (HPLC): 96%
$[\alpha]_D^{20} = +15°$ (C=0.5 MeOH)
M.p. (thermovar): 166°-168° C.
TLC 60 $F_{254}$ silica (MeOH, H$_2$O: 80/20) rf=0.303
IR (KBr): 1670 cm$^{-1}$ (C=O), 1275 cm$^{-1}$, 1580 cm$^{-1}$, 3250 cm$^{-1}$ (N—H)
NMR (200 MHz, CD$_3$OD): 1.55 (3H, d, CH$_3$ala); 2.20 to 2.31 (2H, m, C-2'-H); 3.72 to 3.74 (2H, d, C-5'-H); 3.92 to 3.93 (1H, m, C-4'-H); 4.14 to 4.18 (1H, m, C-ala-H); 4.35 to 4.38 (1H, m, C-3'-H); 6.28 to 6.34 (1H, t, C-1'-H); 8.60 (1H, s, C-6-H).

EXAMPLES 6 TO 17

The following compounds were prepared using experimental procedures analogous to those described in Examples 1 and 2, which those skilled in the art will readily work out:

5'-N-(L-alanyl)amino-2',5'-dideoxy-5-ethyluridine
5'-N-(L-alanyl)amino-2',5'-dideoxy-5-butyluridine
5'-N-(L-alanyl)amino-2',5'-dideoxy-5-propyluridine
5'-N-(L-valyl)amino-2',5'-dideoxy-5-methyluridine
5'-N-(L-leucyl)amino-2',5'-dideoxy-5-methyluridine
5'-N-(sarcosyl)amino-2',5'-dideoxy-5-methyluridine
5'-N-(β-alanyl)amino-2',5'-dideoxy-5-methyluridine
5'-N-(L-alanyl-L-alanyl)amino-2',5'-dideoxy-5-methyluridine
5'-N-(L-alanyl-L-alanyl-L-alanyl)amino-2',5'-dideoxy-5-methyluridine
5'-N-(L-alanyl)amino-2',5'-dideoxy-5-vinyluridine
5'-N-(L-alanyl)amino-2',5'-dideoxy-5-bromovinyluridine

EXAMPLES 18 TO 31

The following compounds were prepared using experimental procedures analogous to those described in Example 3, which those skilled in the art will readily work out:

3'-N-(L-alanyl)amino-2',3'-dideoxy-5-methyluridine
3'-N-(L-alanyl)amino-2',3'-dideoxy-5-ethyluridine
3'-N-(L-alanyl)amino-2',3'-dideoxy-5-butyluridine
3'-N-(L-alanyl)amino-2',3'-dideoxy-5-propyluridine
3'-N-(L-valyl)amino-2',3'-dideoxy-5-methyluridine
3'-N-(L-leucyl)amino-2',3'-dideoxy-5-methyluridine
3'-N-(sarcosyl)amino-2',3'-dideoxy-5-methyluridine
3'-N-(β-alanyl)amino-2',3'-dideoxy-5-methyluridine
3'-N-(L-alanyl-L-alanyl)amino-2',3'-dideoxy-5-methyluridine
3'-N-(L-alanyl-L-alanyl-L-alanyl)amino-2',3'-dideoxy-5-methyluridine
3'-N-(L-glycyl)amino-2',3'-dideoxy-5-methyluridine
3'-N-(L-alanyl)$_6$-amino-2',3'-dideoxy-5-methyluridine
3'-N-(L-alanyl)amino-2',3'-dideoxy-5-vinyluridine
3'-N-(L-alanyl)amino-2',3'-dideoxy-5-bromovinyluridine

EXAMPLES 32 TO 38

The following compounds were prepared using experimental procedures analogous to that described in Example 5, which those skilled in the art will readily work out:

5-N-(L-valyl)amino-2'-deoxyuridine
5-N-(L-leucyl)amino-2'-deoxyuridine
5-N-(sarcosyl)amino-2'-deoxyuridine
5-N-(β-alanyl)amino-2'-deoxyuridine
5-N-(L-alanyl-L-alanyl)amino-2'-deoxyuridine
5-N-(L-alanyl)$_6$-amino-2'-deoxyuridine
5-N-(L-glycyl-L-alanyl)amino-2'-deoxyuridine The activity of the compounds according to the invention as inhibitors of DNA synthesis in cancerous cells was evaluated:
"in vitro" on cytosol FTK (study 1)
"in vivo" on MCF7 cells in culture (study 2)
"in vivo" on immature female WISTAR rats (study 3)

Study 1

Hormone-dependent breast cancer cells (MCF7), which contain 95-96% of fetal thymidine kinase, are treated with ultrasound and centrifuged at 105,000 g.

The MCF7 cells originate from a pleural metastasis of a human breast cancer (Ref. H. SOULE, J. VASQUEZ, A. LONG, S. ALBERT and M. BREUNAN, J. Natl. Cancer Instit., 51, 1409-1416, 1973) and are available for example from the A.T.C.C. (American Type Culture Collection).

The concentration of proteins in the cytosol obtained is measured and adjusted by dilution to 1.5 mg of proteins per ml of cytosol.

The cytosol is incubated at 37° C. for 10 minutes in a Tris buffer (pH: 7.6) in the presence of thymidine [C$^{14}$-2] (40 μmolar), ATP (8 mmolar) and magnesium chloride. The enzymatic reaction is stopped by the addition of perchloric acid.

The nucleotides formed are separated by high-voltage electrophoresis and the blots are cut out and counted.

Table 1 gives the results of the tests performed with the compounds of Examples 1 and 2 and, by way of comparison, with inhibitor-free control compounds.

The values given are expressed in picomol per milliliter of cytosol per minute.

TABLE 1

| Compound | Concentration | TMP + TTP | TTP |
|---|---|---|---|
| (Control) | no inhibitor | 1993 | 1573 |
| Ex. 1 | 1 mmolar | 1329 | 38 |
| (Control) | no inhibitor | 486 | 368 |
| Ex. 2 | 1 mmolar | 388 | 46 |

This biochemical test is based on knowledge of the fact that thymidine kinase occupies a strategic position in biochemical processes culminating in DNA synthesis using thymidine triphosphate (TTP), which can be considered as the final product of a complex reaction initiated by thymidine kinase.

As shown in Table 1, the compounds according to the invention act as inhibitors of TTP synthesis and hence probably of DNA synthesis in proliferating cancerous cells.

Study 2

Culture of MCF-7 cells

MCF-7 cells are cultivated in 75 cm$^2$ flasks. Each flask is inoculated with $0.6 \times 10^6$ cells suspended in 10 ml of RPMI-1640 medium to which 2 mM of L-glutamine, 2.5 μg/ml of Fungizone, 15 U/ml of penicillin, 50 μg/ml of streptomycin and 5% of fetal calf serum are added.

The cells are cultivated for 72 hours at 37° C. in a $CO_2$ incubator (EG 110, IR. Jouan). The culture media are changed every 48 hours.

The cells are harvested by detachment using a rubber policeman and the cell suspension is centrifuged at 200 g in a cooled centrifuge to give a cell residue.

Inhibitor tests

The different inhibitors to be tested are dissolved in RPMI-1640 at a concentration of 1 mM. Their effects are tested for 48 and 72 hours.

Analytical tests

Counting of the cells: The cell lawns are washed 3 times with 5 ml of a phosphate buffered saline (PBS). The contents of each culture flask are then suspended in 10 ml of PBS. The cells are counted by means of an H. C. 202$^R$ Hycel Counter.

Assay of the DNA: This is carried out on an aliquot of the cell sonicate by spectrofluorimetry according to the technique of C. Brunk et al., Analyst. Biochem., 92, 497–500, 1979.

TABLE 2

| | 48 h | | 72 h | |
|---|---|---|---|---|
| | Cells × $10^6$/dish | DNA μg/dish | Cells × $10^6$/dish | DNA μg/dish |
| Control compounds | 2.41 | 47.4 | 5.03 | 89.8 |
| Example 1 | 0.60 | 8.1 | 0.43 | 2.5 |
| Example 2 | 1.50 | 22.7 | 3.60 | 56.5 |
| Example 4 | 1.20 | 16.2 | 2.55 | 34.8 |

Study 3

Protocol

Animals

22-Day-old female WISTAR rats (IFFA CREDO) with a mean weight of between 30 and 50 g.

They are separated from the mother 2 days before the start of the test.

They have free access to food and drinking water throughout the test.

Products 0.9% NaCl

Absolute alcohol

17β-Estradiol dipropionate (Sigma reference E.9125)

A solution containing 2 mg.ml$^{-1}$ in 0.9% NaCl is prepared.

6-[$^3$H]-Deoxythymidine (Amersham reference TRK61 at 24 Ci/mmol)

The working solution is prepared by diluting the commercial solution to 1/11. Its volume activity is 10 μCi/0.1 ml.

Example 1

Example 2

These products are dissolved in 0.9% NaCl for administration of a volume of 0.1 ml/animal.

| NaOH | 5 ml |
|---|---|
| $HClO_4$ | 0.6 N |
| KOH | 0.6 N |

Diphenylamine (Sigma reference D.2285) in solution in glacial acetic acid (1%)

Concentrated $H_2SO_4$

Calf thymus DNA (Boehringer reference 104 175) in solution in 5 mM NaOH

Instage ®

Procedure

1. Treatments and sacrifice

These operations are carried out according to the following scheme:

```
        t0              t23h            t24h
        |               |               |
    Estradiol       +[³H]-dTh       Sacrifice
    or NaCl         inhibitor
```

| t0 | The "Absolute Control" group receives 0.1 ml of 0.9% NaCl by intraperitoneal administration. The other groups receive 800 ng/animal of estradiol in a volume of 0.1 ml. |
|---|---|
| t23h | All the animals receive 10 μCi of [$^3$H]-dTh in a volume of 0.1 ml by intraperitoneal administration.<br>The "Estradiol Control" group and the "Absolute Control" group receive 0.1 ml of 0.9% NaCl.<br>The "Inhibitors" groups receive the test products in a volume of 0.1 ml by intraperitoneal administration. |
| t24h | All the animals are sacrificed by dislocation of the neck. The uteri are removed, wiped on filter paper, weighed and frozen. |

2. Treatment of the uteri

The uterus is ground in 0.5 ml of 0.6N perchloric acid in a Potter mill. The piston of the mill is rinsed 3 times with 0.3 ml of 0.6N perchloric acid.

The homogenate and the rinsing liquors are combined in conical glass tubes and then centrifuged at 800 g for 10 minutes. The residue is washed twice with 1 ml of 0.3N perchloric acid.

This residue is taken up with 0.6 ml of 0.3N KOH; the tubes are placed in a water bath at 37° C. for 2 hours 30 minutes.

After alkaline hydrolysis (hydrolysis of the RNA), 30 μl of 11N perchloric acid are added in order to precipitate the DNA.

The tubes are cooled in ice and then centrifuged at 4200 g for 10 minutes.

The residue is washed twice with 1 ml of 0.3N perchloric acid. The last residue is taken up with 0.6 ml of 0.6N perchloric acid. The tubes are heated at 80° C. for 10 minutes. After cooling in ice for a few minutes, they are centrifuged for 10 minutes at 4200 g.

3. Determination of the radioactivity incorporated in the DNA

50 μl of supernatant are placed in counting flasks.

After the addition of 5 ml of Instagel, counting is carried out over 10 minutes.

The c.p.m. (counts per minute) are converted to d.p.m.:

$$d.p.m = \frac{c.p.m.}{E} \quad (d.p.m. = \text{disintergrations per minute})$$

E = counting efficiency = 0.37

The d.p.m. in picomol of [$^3$H]-dTh according to the $$\text{formula} \frac{d.p.m.}{2220 \times 25}$$

Specific activity of the [$^3$H]-dTh: 25 nCi/picomol 1 nCi = 2220 d.p.m.

The results are expressed in pmol of deoxythymidine incorporated per uterus.

4. Assay of the DNA 1.2 ml of a solution of diphenylamine in glacial acetic acid (1 g/100 ml) are added to 100 μl of supernatant diluted to 1/6 in 0.6N perchloric acid.

The tubes are placed in a boiling water bath for 10 minutes. After cooling, the optical density is read off at 595 nm. Calibration is effected with the aid of a solution of calf thymus DNA.

The results are expressed in μg/uterus.

TABLE 3

|  | Weight of the uteri mg | DNA μg/uterus | $^3$H-dTh pmol/uterus |
|---|---|---|---|
| Control compound (n = 8) | 33.1 ± 1.2 | 273 ± 18 | 0.189 ± 0.004 |
| Estradiol (n = 8) | 44.4 ± 5.4 | 371 ± 49 | 1.133 ± 0.244 |
| Estradiol + Example 1 10 mg · kg$^{-1}$ (n = 8) | 55.2 ± 4.9 | 383 ± 32 | 0.735 ± 0.152 |
| Estradiol + Example 2 10 mg · kg$^{-1}$ (n = 8) | 54.5 ± 3.9 | 360 ± 17 | 0.708 ± 0.165 |

What is claimed is:

1. A 2'-deoxyuridine having the formula:

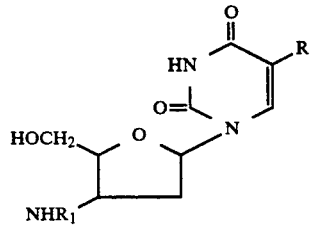

wherein R is selected from the group consisting of alkyl moieties having from one to four carbon atoms, alkenyl moieties having from two to four carbon atoms, halogens and halogenated alkenyl moieties having from two to four carbon atoms; and R$_1$ is an amino acid residue or a peptide residue containing from two to six amino acids; and the pharmaceutically acceptable salts of said compound.

2. The compound of claim 1, wherein said amino acid or peptide reside is in the L or D form.

3. 3'-N-(L-alanyl) amino-2',3'-dideoxy-5-methyluridine.

4. 3'-N-(D-alanyl) amino-2',3'-dideoxy-5-methyluridine.

5. A pharmaceutical composition active as an inhibitor of DNA synthesis in proliferating cancerous cells comprising an effective amount of an active ingredient comprising the compound of claim 1 or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO.  :   5,212,161
DATED       :   May 18, 1993
INVENTOR(S) :   Moriniere et al.

It is certified that error appears in the above-identified patent and that said Letters Patent is hereby corrected as shown below:

On the title page, item [54] and in column 1, line 4, in the title
 "α-AMINACYL" should read --α-AMINOACYL--.
Column 1, line 5, "α-AMINACYL" should read --α-AMINOACYL--.
Column 1, line 43, after "of the formula" insert the following formula:

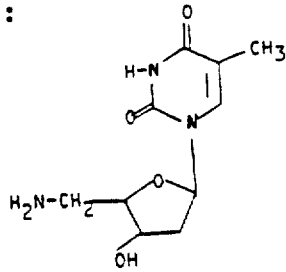

Column 3, line 45, "DL foam" should read --DL form--.
Column 5, lines 52-53, "palladium-oncharcoal" should read --palladium-on-charcoal--.
Column 7, lines 48-49, "palladiu-mon-charcoal" should read --palladium-on-charcoal--.
Column 14, claim 2, line 2, "reside" should read --residue--.

Signed and Sealed this

First Day of February, 1994

Attest:

BRUCE LEHMAN

*Attesting Officer*     Commissioner of Patents and Trademarks